(12) United States Patent
Shao et al.

(10) Patent No.: US 11,464,746 B2
(45) Date of Patent: Oct. 11, 2022

(54) METHOD FOR PREPARING ELECTROSPRAYING PARTICLES TO IMPROVE STABILITY OF POLYPHENOL

(71) Applicant: Zhejiang University of Technology, Hangzhou (CN)

(72) Inventors: Ping Shao, Hangzhou (CN); Ben Niu, Hangzhou (CN); Ligang Jiang, Hangzhou (CN)

(73) Assignee: Zhejiang University of Technology, Hangzhou (CN)

( * ) Notice: Subject to any disclaimer, the term of this patent is extended or adjusted under 35 U.S.C. 154(b) by 812 days.

(21) Appl. No.: 16/419,323

(22) Filed: May 22, 2019

(65) Prior Publication Data
US 2020/0368168 A1 Nov. 26, 2020

(51) Int. Cl.
| | |
|---|---|
| A61K 36/00 | (2006.01) |
| A61K 9/48 | (2006.01) |
| A23L 33/11 | (2016.01) |
| A23P 10/30 | (2016.01) |
| A23L 29/294 | (2016.01) |
| B01J 2/02 | (2006.01) |
| A23L 29/231 | (2016.01) |

(52) U.S. Cl.
CPC .......... *A61K 9/4833* (2013.01); *A23L 29/231* (2016.08); *A23L 29/294* (2016.08); *A23L 33/11* (2016.08); *A23P 10/30* (2016.08); *A61K 9/4816* (2013.01); *B01J 2/02* (2013.01); *A23V 2002/00* (2013.01)

(58) Field of Classification Search
CPC .................................................. A23L 29/231
See application file for complete search history.

(56) References Cited

FOREIGN PATENT DOCUMENTS

| | | | |
|---|---|---|---|
| CN | 101856604 A | | 10/2010 |
| CN | 103668485 A | | 3/2014 |
| CN | 105126770 A | * | 12/2015 |

* cited by examiner

*Primary Examiner* — Qiuwen Mi
(74) *Attorney, Agent, or Firm* — Schwegman Lundberg & Woessner, P.A.

(57) ABSTRACT

This invention provides a method for preparing electrospraying particles to improve stability of polyphenol including the following steps: preparing a pectin-silica composite; adding polyphenolic compounds into the pectin-silica composite to prepare a core solution; and coaxial electrospraying the core solution and a shell solution to prepare electrospraying particles loaded polyphenol. This method utilizes a pectin-silica composite as a polyphenol loading carrier, improves the encapsulating efficiency of polyphenols, reduces the contact probability of polyphenols with oxygen and water, and improves the stability of polyphenols; and an acidic aqueous solution is used as a shell solution to synergize with the pectin-silica composite to further improve the stability of polyphenols.

8 Claims, 1 Drawing Sheet

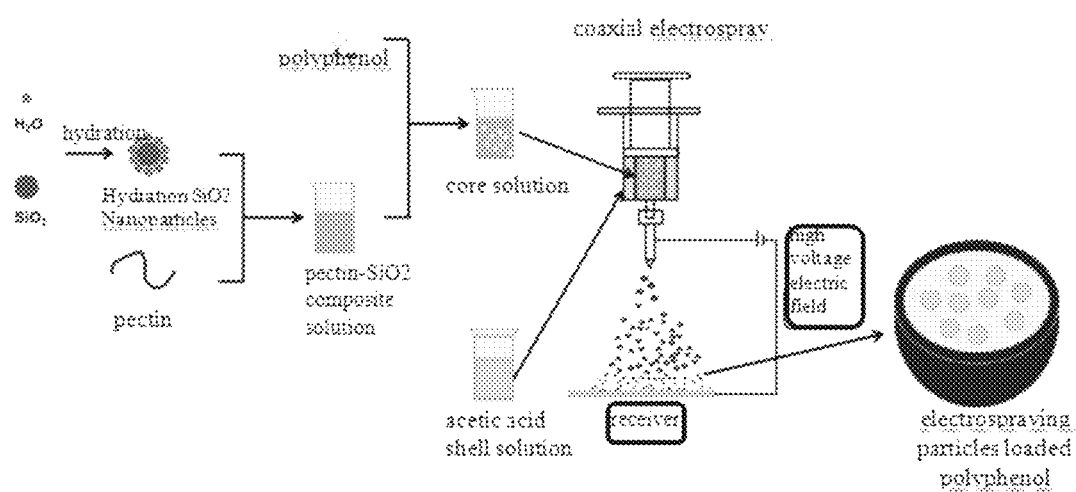

METHOD FOR PREPARING ELECTROSPRAYING PARTICLES TO IMPROVE STABILITY OF POLYPHENOL

BACKGROUND OF THE INVENTION

Field of the Invention

This invention relates to a technical field of polymer chemistry and food and, more particularly, to a method for preparing electrospraying particles to improve stability of polyphenol.

Description of the Related Art

Polyphenols are secondary metabolites presented in the leaves of many higher plants and fruits. More than 8000 polyphenols have been identified. Although polyphenols are regarded as non-nutrient xenobiotics, they have various biological activities, including antioxidant and anti-inflammatory effects, prevention of neurological, cardiovascular and chronic intestinal diseases, diabetes and Alzheimer's disease, and improvement of memory and cognitive function. Although polyphenolic compounds have many excellent biological functions, they are easy to be destroyed by the digestive system in vivo, thereby losing their activity. For example, they are easy to be oxidized under the environment of strong acid, strong base and high temperature. Therefore, it is necessary to develop a carrier for encapsulating polyphenols in order to maintain their biological activity.

Electrospraying is a method for making a polymer solution or melt into micro-particles, nano-particles or fibrous materials by using electrohydrodynamic technology. By adjusting various parameters of electrospraying device, micro-particles, nano-particles or fibrous materials can be prepared. During electrospraying, electrostatic force overcomes the surface tension of polymer droplets, and the liquid jet breaks down into small droplets, thereby forming micro-particles and nano-particles. Electrospraying has many advantages, such as making micro-particles and nano-particles with uniform size, easy processing parameters to achieve the required particle size and morphology, and rapid and one-step synthesis of particles without additional drying steps (such as emulsion solvent evaporation and nanoprecipitation). During the preparation of electrospraying particles, barrier properties of the electrospraying substrate (polymer) are important factors affecting the encapsulating efficiency and stability of the active factor. As natural polysaccharides and proteins contain a large number of hydrophilic groups, water vapor and oxygen can be rapidly contacted with active factors through diffusion. At the same time, due to the large specific surface area of electrospraying particles, the exposure probability of polyphenols is increased, leading to poor stability of polyphenols.

A patent with the announcement number of CN 101856604 A discloses a method for preparing probiotic microcapsules by electrospraying. In this method, probiotic microcapsules were prepared by electrospraying with alginate and gelatin used as wall material, probiotics suspension or microporous starch adsorbed probiotics used as core material and calcium chloride used as curing agent. However, it is easy to cause blockage of the nozzle as this method is simple to mix the wall material and core material. Moreover, as only natural polymers are used, the protection of probiotic storage stability is insufficient.

A patent with the announcement number of CN 103668485 B discloses a method for preparing nanofiber loaded bio-enzymes by coaxial three-layer electrospinning. However, the polyvinyl alcohol, polyacrylic acid, polyvinylpyrrolidone or polyacrylamide used in this method are all synthetic polymers, which have some potential safety hazards, and the operation is complicate.

Therefore, the method for preparing the electrospraying particles to improve the stability of the polyphenol is needed on the market. The existing technology cannot solve such problems, and this invention can solve such problems.

BRIEF SUMMARY OF THE INVENTION

In order to solve the deficiencies of the prior art, the objective of this invention is to provide a method for preparing electrospraying particles to improve stability of polyphenol. This method utilizes a pectin-silica composite as a polyphenol loading carrier, improves the encapsulating efficiency of polyphenols, reduces the contact probability of polyphenols with oxygen and water, and improves the stability of polyphenols; and an acidic aqueous solution is used as a shell solution to synergize with the pectin-silica composite to further improve the stability of polyphenols.

In order to achieve the above-mentioned objective, the following technical solution is adopted in this invention.

A method for preparing electrospraying particles to improve stability of polyphenol includes the following steps:

preparing a pectin-silica composite;

adding polyphenolic compounds into the pectin-silica composite to prepare a core solution; and coaxial electrospraying the core solution and a shell solution to prepare electrospraying particles loaded polyphenol.

The above-mentioned method for preparing the electrospraying particles to improve the stability of the polyphenol, wherein preparing the pectin-silica composite includes the following steps:

preparing a pectin solution: adding deionized water into pectin and stirring until the pectin is completely dissolved, and the pectin solution in an amount of 5%-10% by weight is prepared;

preparing a silica suspension: adding the deionized water into a silica powder while stirring, and the silica suspension in an amount of 0.1%-0.5% by weight is prepared; and preparing the pectin-silica composite: adding the silica suspension in the amount of 0.1%-0.5% by weight into the pectin solution in the amount of 5%-10% by weight drop by drop while stirring, and the pectin-silica composite being obtained.

The above-mentioned method for preparing the electrospraying particles to improve the stability of the polyphenol, add 0.1-0.5 g tea polyphenols into the pectin-silica composite and stir, and the core solution is prepared.

The above-mentioned method for preparing the electrospraying particles to improve the stability of the polyphenol, wherein the shell solution is an acidic aqueous solution.

The above-mentioned method for preparing the electrospraying particles to improve the stability of the polyphenol, wherein the shell solution is the acidic aqueous solution of which pH is 4.

The above-mentioned method for preparing the electrospraying particles to improve the stability of the polyphenol, wherein the shell solution is an acetic acid solution in an amount of 5%-10%.

The above-mentioned method for preparing the electrospraying particles to improve the stability of the polyphenol, wherein electrospraying conditions include: electrostatic voltage: 16-18 kv; receiving distance: 13-16 cm; needle type of the core solution: inner diameter 0.6 mm, outer diameter 0.9 mm; needle type of the shell solution: inner diameter 0.12 mm, outer diameter 0.15 mm; room temperature: 20° C.-25° C.; and air humidity: 45%-65%.

The above-mentioned method for preparing the electrospraying particles to improve the stability of the polyphenol includes the following steps:

preparing a pectin solution: adding deionized water into pectin and stirring until the pectin is completely dissolved, and the pectin solution in an amount of 10% by weight being prepared;

preparing a silica suspension: adding the deionized water into a silica powder while stirring, and the silica suspension in an amount of 0.5% by weight being prepared;

adding 0.5 g tea polyphenols into the pectin-silica composite and stirring for 2 hours in a magnetic stirrer, and the pectin-silica composite being prepared; and placing the pectin-silica composite on an electrospraying device as the core solution, taking an acetic acid solution in an amount of 10% by weight as the shell solution, and electrospraying particles loaded polyphenol being prepared;

wherein electrospraying conditions include: electrostatic voltage: 18 kv; receiving distance: 16 cm; needle type of the core solution: inner diameter 0.6 mm, outer diameter 0.9 mm; needle type of the shell solution: inner diameter 0.12 mm, outer diameter 0.15 mm; room temperature: 25° C.; and air humidity: 65%.

The advantages of this invention lie in:

In this invention, the pectin-silica composite is taken as the polyphenol loading carrier, the stability of polyphenols is improved by increasing the encapsulating efficiency of polyphenols and reducing the contact probability of polyphenols with oxygen and water.

In acidic environment, the pectin-silica composite solution loaded with polyphenols can be evaporated evenly. By slowing down the formation of semi-solid state on the surface of droplets, acidic aqueous solution helps polymer molecules to diffuse into droplets, thereby eliminating the potential collapse of particles, such that round particles with round surfaces and compact interiors are produced, and the distribution of polyphenols on the surface of droplets is reduced. On the other hand, for the acidic aqueous solution, the distribution state of the silica electrospraying particles is adjusted by adjusting the intensity of interaction between silica molecules and hydrogen bonds between silica and pectin. When the solution of which pH is 4 is used, the silica exhibits a homogenous distribution state, which can improve the barrier property of pectin to water vapor and oxygen, thereby improving the stability of polyphenols. After 50 days, the retention rate of polyphenols when the pectin-silica is taken as the carrier can reach more than 70% compared with the retention rate of 42.2% while polyphenol in the pectin electrospraying particles.

BRIEF DESCRIPTION OF THE DRAWINGS

FIG. 1 is a preparation flowchart of an embodiment of this invention.

DETAILED DESCRIPTION OF THE INVENTION

This invention is specifically described below with reference to the accompanying drawings and specific embodiments.

As shown in FIG. 1, a method for preparing electrospraying particles to improve stability of polyphenol includes the following steps.

Step One Prepare a Pectin-Silica Composite

Preparing the pectin-silica composite includes the following steps: preparing a pectin solution: adding deionized water into pectin and stirring until the pectin is completely dissolved, and the pectin solution in an amount of 5%-10% by weight being prepared;

preparing a silica suspension: adding the deionized water into a dry silica powder while stirring, and the silica suspension in an amount of 0.1%-0.5% by weight being prepared; and preparing a pectin-silica composite: adding the silica suspension in the amount of 0.1%-0.5% by weight into the pectin solution in the amount of 5%-10% by weight drop by drop while stirring, and the pectin-silica composite being obtained.

Step Two add polyphenolic compounds into the pectin-silica composite to prepare a core solution. As one embodiment, polyphenolic compounds are tea polyphenols. Add 0.1-0.5 g tea polyphenols into the pectin-silica composite and stir, and the core solution is prepared. It should be noted that water-soluble polyphenols are applicable to this invention.

Step Three coaxial electrospray the core solution and a shell solution to prepare electrospraying particles loaded polyphenol.

As a preferred way, the shell solution is an acidic aqueous solution. Further preferably, the shell solution is the acidic aqueous solution of which pH is 4. As one embodiment, the shell solution is an acetic acid solution in an amount of 5%-10%.

Electrospraying conditions include: electrostatic voltage: 16-18 kv; receiving distance: 13-16 cm; needle type of the core solution: inner diameter 0.6 mm, outer diameter 0.9 mm; needle type of the shell solution: inner diameter 0.12 mm, outer diameter 0.15 mm; room temperature: 20° C.-25° C.; and air humidity: 45%-65%.

Principles:

(1) In this invention, the pectin-silica composite is taken as the polyphenol loading carrier, the stability of polyphenols is improved by increasing the encapsulating efficiency of polyphenols and reducing the contact probability of polyphenols with oxygen and water.

Specifically, due to the concentration of the solution used for electrospraying is relatively low, the concentration of the chain entanglement of pectin molecules in solution is insufficient. After the silica contacts with water, the surface of the silica forms hydrated layer with hydroxyl groups, which is bonded to the pectin through hydrogen bonds. A silica molecule is connected with several pectin molecules, which increases the number of entanglement of pectin molecules, enhances the stability of "Tylor cone" during electrospraying process, and improves the encapsulating efficiency of polyphenols. Taking the pectin-silica composite as wall material, on one hand, nano-fillers cause the "tortuous path" and "permeability area reduction" effect of small molecules. On the other hand, the addition of silica increases the relative crystallinity of pectin, reduces the frequency of movement of the pectin molecular chain, reduces the penetration rate of water molecules and oxygen, improves the barrier property of pectin to water vapor and oxygen, reduces the contact probability of polyphenols with oxygen and water, and improves the stability of polyphenols. Compared with the water vapor transmission rate ($6.174 \times 10^{-11}$ g/m s Pa) and oxygen transmission rate ($3.762 \times 10^{-3}$ g/m$^2$ s)

of pectin electrospraying particles, the water vapor transmission rate of pectin silica polymer is reduced to below $3.0\times10^{-11}$ g/m s Pa, and the oxygen transmission rate is reduced to $2.8\times10^{-3}$ g/m$^2$ s.

(2) In this invention, the acidic aqueous solution is taken as the shell solution, the pectin-silica composite and the polyphenol solution are taken as the core solution, coaxial electrospraying is used to encapsulate the polyphenol, and the stability of polyphenols is improved.

Specifically, when the acidic aqueous solution is used as the shell solution, its low viscosity favors Coulomb fission, and the entire droplet is uniformly and completely dried. In acidic environment, the pectin-silica composite solution loaded with polyphenols can be evaporated evenly. By slowing down the formation of semi-solid state on the surface of droplets, acidic aqueous solution helps polymer molecules to diffuse into droplets, thereby eliminating the potential collapse of particles, such that round particles with round surfaces and compact interiors are produced, and the distribution of polyphenols on the surface of droplets is reduced. On the other hand, for the acidic aqueous solution, the distribution state of the silica electrospraying particles is adjusted by adjusting the intensity of interaction between silica molecules and hydrogen bonds between silica and pectin. Synergistic effect of acidic aqueous solution and pectin-silica composite further improves the stability of polyphenols. After 50 days, the retention rate of polyphenols when the pectin-silica is taken as the carrier can reach more than 70% compared with the retention rate of 42.2% while polyphenol in the pectin electrospraying particles.

The following experiments verify the effect.

Embodiment One (1) preparing a pectin solution: adding deionized water into pectin and stirring in a magnetic stirrer until the pectin is completely dissolved, and the pectin solution in an amount of 5% by weight being prepared;

(2) preparing a silica suspension: adding the deionized water into a dry silica powder while stirring, and the silica suspension in an amount of 0.1% by weight being prepared;

(3) preparing a pectin-silica composite: adding the above-mentioned silica suspension into the pectin solution drop by drop while stirring, and the pectin-silica composite being prepared;

(4) adding 0.1 g tea polyphenols into the pectin-silica composite and stirring for 2 hours in the magnetic stirrer; and (5) placing the solution prepared in step (4) on an electrospraying device as a core solution, taking an acetic acid solution in an amount of 5% by weight as a shell solution, and electrospraying particles loaded polyphenol 1 being prepared; wherein electrospraying conditions include: electrostatic voltage: 16 kv; receiving distance: 13 cm; needle type of the core solution: inner diameter 0.6 mm, outer diameter 0.9 mm; needle type of the shell solution: inner diameter 0.12 mm, outer diameter 0.15 mm; room temperature: 20° C.; and air humidity: 45%.

Embodiment Two (1) preparing a pectin solution: adding deionized water into pectin and stirring in a magnetic stirrer until the pectin is completely dissolved, and the pectin solution in an amount of 10% by weight being prepared;

(2) preparing a silica suspension: adding the deionized water into a dry silica powder while stirring, and the silica suspension in an amount of 0.5% by weight being prepared;

(3) preparing a pectin-silica composite: adding the above-mentioned silica suspension into the pectin solution drop by drop while stirring, and the pectin-silica composite being prepared;

(4) adding 0.5 g tea polyphenols into the pectin-silica composite and stirring for 2 hours in the magnetic stirrer; and (5) placing the solution prepared in step (4) on an electrospraying device as a core solution, taking an acetic acid solution in an amount of 10% by weight as a shell solution, and electrospraying particles loaded polyphenol 2 being prepared; wherein electrospraying conditions include: electrostatic voltage: 18 kv; receiving distance: 16 cm; needle type of the core solution: inner diameter 0.6 mm, outer diameter 0.9 mm; needle type of the shell solution: inner diameter 0.12 mm, outer diameter 0.15 mm; room temperature: 25° C.; and air humidity: 65%.

Embodiment Three (1) preparing a pectin solution: adding deionized water into pectin and stirring in a magnetic stirrer until the pectin is completely dissolved, and the pectin solution in an amount of 8% by weight being prepared;

(2) preparing a silica suspension: adding the deionized water into a dry silica powder while stirring, and the silica suspension in an amount of 0.3% by weight being prepared;

(3) preparing a pectin-silica composite: adding the above-mentioned silica suspension into the pectin solution drop by drop while stirring, and the pectin-silica composite being prepared;

(4) adding 0.3 g tea polyphenols into the pectin-silica composite and stirring for 2 hours in the magnetic stirrer; and (5) placing the solution prepared in step (4) on an electrospraying device as a core solution, taking an acetic acid solution in an amount of 8% by weight as a shell solution, and electrospraying particles loaded polyphenol 3 being prepared;

wherein electrospraying conditions include: electrostatic voltage: 18 kv; receiving distance: 15 cm; needle type of the core solution: inner diameter 0.6 mm, outer diameter 0.9 mm; needle type of the shell solution: inner diameter 0.12 mm, outer diameter 0.15 mm; room temperature: 25° C.; and air humidity: 65%.

Embodiment Four (1) preparing a pectin solution: adding deionized water into pectin and stirring in a magnetic stirrer until the pectin is completely dissolved, and the pectin solution in an amount of 10% by weight being prepared;

(2) preparing a silica suspension: adding the deionized water into a dry silica powder while stirring, and the silica suspension in an amount of 0.5% by weight being prepared;

(3) preparing a pectin-silica composite: adding the above-mentioned silica suspension into the pectin solution drop by drop while stirring, and the pectin-silica composite being prepared;

(4) adding 0.5 g tea polyphenols into the pectin-silica composite and stirring for 2 hours in the magnetic stirrer; and (5) placing the solution prepared in step (4) on an electrospraying device as a core solution, and electrospraying particles loaded polyphenol 4 being prepared; wherein electrospraying conditions include: electrostatic voltage: 18 kv; receiving distance: 16 cm; needle type of the core solution: inner diameter 0.6 mm, outer diameter 0.9 mm; needle type of the shell solution: inner diameter 0.12 mm, outer diameter 0.15 mm; room temperature: 25° C.; and air humidity: 65%.

Compared with Embodiment Two, Embodiment Four does not use the acidic aqueous solution as the shell solution for coaxial electrospraying.

Samples 1-4 and pectin electrospraying particles are separately subjected to barrier property experiments and polyphenol retention rate experiments.

Experiment of water vapor transmission rate: the electrospraying particles are made into a wafer with a diameter of 2.5 cm by using the tablet press machine and are sealed at the test cup. In the test cup, 3 g anhydrous $CaCl_2$ is placed, and then the cup is placed in the environment with relative humidity (RH) of 90% and temperature of 40 C. The weight of the cup is tested every 1.5 h for 24 h. Then the water vapor transmission rate is calculated according to formula 1.

$$WVP = \frac{\Delta m \times d}{A \times \Delta t \times \Delta P}$$

In the formula, WVP is the water vapor transmission rate ($\times 10^{-11}$ g/m s Pa), $\Delta m$ is the weight gain of the cup (g), d is the thickness of the electrospraying particle wafer (m), A is the area of the wafer (m2), $\Delta t$ is the test time (s), and $\Delta P$ is the internal and external water vapor pressure difference (Pa) of the membrane Experiment of oxygen transmission rate: the electrospraying particles are made into a diameter of 2.5 cm by using the tablet press machine and are sealed at the test cup. 1 g iron powder, 2 g activated carbon, and 3 g NaCl are placed in the cup. and then the cup is placed in the environment with relative humidity (RH) of 75% and temperature of 25 C for 48 h. Then the oxygen transmission rate is calculated according to formula 2.

$$OP = \frac{m - m_0}{A \times t}$$

In the formula, OP is the oxygen transmission rate ($\times 10^{-3}$ g/m² s), m is the mass of the cup after oxygen adsorption (g), $m_0$ is the original mass of the cup (g), A is the area of the wafer (m²), and t is the test time (s).

Experiment of polyphenol retention rate: 5 g electrospraying particles are placed in the environment with relative humidity (RH) of 90% and temperature of 30° C. The content of polyphenols in 1 g electrospraying particles is determined by high performance liquid chromatography every ten days. The first determination of polyphenol content is taken as the standard, which is recorded as 100% the retention rate of polyphenols, and then the retention rate of polyphenols in subsequent particles is calculated according to formula 3.

$$R\% = \frac{m}{m_0} \times 100\%$$

In the formula, m is the polyphenol content in electrospraying particles after storage, and $m_0$ is the polyphenol content in the initial electrospraying particles.

The experimental results are shown in Table 1.

TABLE 1

Barrier properties of different samples

| | water vapor transmission rate ($\times 10^{-11}$ g/m s Pa) | oxygen transmission rate ($\times 10^{-3}$ g/m² s) |
|---|---|---|
| Pectin electrospraying particles | 6.174 | 3.762 |
| Sample 1 | 2.985 | 2.842 |
| Sample 2 | 3.072 | 2.762 |
| Sample 3 | 2.868 | 2.821 |
| Sample 4 | 4.618 | 3.484 |

As can be seen from the results in Table 1, the addition of silica increases the relative crystallinity of pectin, reduces the frequency of movement of the pectin molecular chain, reduces the penetration rate of water molecules and oxygen, improves the barrier property of pectin to water vapor and oxygen, reduces the contact probability of polyphenols with oxygen and water, and improves the stability of polyphenols.

TABLE 2

Effects of different polymer carriers on the retention rate of polyphenols

| | 10 d | 20 d | 30 d | 40 d | 50 d |
|---|---|---|---|---|---|
| Pectin electrospraying particles | 100% | 83.1% | 62.5% | 51.8% | 42.2% |
| Sample 1 | 100% | 92.6% | 85.7% | 79.7% | 72.3% |
| Sample 2 | 100% | 96.4% | 87.6% | 80.6% | 71.6% |
| Sample 3 | 100% | 94.3% | 86.2% | 80.1% | 72.9% |
| Sample 4 | 100% | 81.2% | 74.8% | 65.4% | 57.5% |

From the above table, it can be known that the acidic aqueous solution and pectin-silica composite have synergistic effect on the stability of polyphenol. After 50 days, the retention rate of polyphenols when the pectin-silica is taken as the carrier can reach more than 70% compared with the retention rate of 42.2% while polyphenol in the pectin electrospraying particles.

In this invention, the pectin-silica composite is taken as the polyphenol loading carrier, the stability of polyphenols is improved by increasing the encapsulating efficiency of polyphenols and reducing the contact probability of polyphenols with oxygen and water. In acidic environment, the pectin-silica composite solution loaded with polyphenols can be evaporated evenly. By slowing down the formation of semi-solid state on the surface of droplets, acidic aqueous solution helps polymer molecules to diffuse into droplets, thereby eliminating the potential collapse of particles, such that round particles with round surfaces and compact interiors are produced, and the distribution of polyphenols on the surface of droplets is reduced. On the other hand, for the acidic aqueous solution, the distribution state of the silica electrospraying particles is adjusted by adjusting the intensity of interaction between silica molecules and hydrogen bonds between silica and pectin. Synergistic effect of acidic aqueous solution and pectin-silica composite further improves the stability of polyphenols.

The basic principles, main features and advantages of this invention are shown and described above. Those skilled in the prior art should understand that the above-mentioned embodiments do not restrict the invention in any form, and any technical solutions obtained by equivalent substitution or equivalent transformation falls within the protection scope of this invention.

What is claimed is:

1. A method for preparing electrospraying particles to improve stability of polyphenol comprising the following steps:
preparing a pectin-silica composite;
adding polyphenolic compounds into the pectin-silica composite to prepare a core solution; and
coaxial electrospraying the core solution and a shell solution to prepare electrospraying particles loaded polyphenol.

2. The method for preparing the electrospraying particles to improve the stability of the polyphenol according to claim 1, wherein preparing the pectin-silica composite comprising the following steps:
preparing a pectin solution: adding deionized water into pectin and stirring until the pectin is completely dissolved, and the pectin solution in an amount of 5%-10% by weight is prepared;
preparing a silica suspension: adding the deionized water into a silica powder while stirring, and the silica suspension in an amount of 0.1%-0.5% by weight is prepared; and
preparing the pectin-silica composite: adding the silica suspension in the amount of 0.1%-0.5% by weight into the pectin solution in the amount of 5%-10% by weight drop by drop while stirring, and the pectin-silica composite being obtained.

3. The method for preparing the electrospraying particles to improve the stability of the polyphenol according to claim 2, adding 0.1-0.5 g tea polyphenols into the pectin-silica composite and stirring, and the core solution being prepared.

4. The method for preparing the electrospraying particles to improve the stability of the polyphenol according to claim 1, wherein the shell solution is an acidic aqueous solution.

5. The method for preparing the electrospraying particles to improve the stability of the polyphenol according to claim 4, wherein the shell solution is the acidic aqueous solution of which pH is 4.

6. The method for preparing the electrospraying particles to improve the stability of the polyphenol according to claim 4, wherein the shell solution is an acetic acid solution in an amount of 5%-10%.

7. The method for preparing the electrospraying particles to improve the stability of the polyphenol according to claim 1, wherein electrospraying conditions comprise: electrostatic voltage: 16-18 kv; receiving distance: 13-16 cm; needle type of the core solution: inner diameter 0.6 mm, outer diameter 0.9 mm; needle type of the shell solution: inner diameter 0.12 mm, outer diameter 0.15 mm; room temperature: 20° C.-25° C.; and air humidity: 45%-65%.

8. The method for preparing the electrospraying particles to improve the stability of the polyphenol according to claim 1, comprising the following steps:
preparing a pectin solution: adding deionized water into pectin and stirring until the pectin is completely dissolved, and the pectin solution in an amount of 10% by weight being prepared;
preparing a silica suspension: adding the deionized water into a silica powder while stirring, and the silica suspension in an amount of 0.5% by weight being prepared;
adding 0.5 g tea polyphenols into the pectin-silica composite and stirring for 2 hours in a magnetic stirrer, and the pectin-silica composite being prepared; and
placing the pectin-silica composite on an electrospraying device as the core solution, taking an acetic acid solution in an amount of 10% by weight as the shell solution, and electrospraying particles loaded polyphenol being prepared;
wherein electrospraying conditions comprise: electrostatic voltage: 18 kv; receiving distance: 16 cm; needle type of the core solution: inner diameter 0.6 mm, outer diameter 0.9 mm; needle type of the shell solution: inner diameter 0.12 mm, outer diameter 0.15 mm; room temperature: 25° C.; and air humidity: 65%.

* * * * *